(12) United States Patent
Hiles

(10) Patent No.: US 8,992,485 B2
(45) Date of Patent: Mar. 31, 2015

(54) DRUG DELIVERY DEVICES AND METHOD OF ASSEMBLY

(75) Inventor: John Hiles, South Wirral (GB)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 341 days.

(21) Appl. No.: 13/504,057

(22) PCT Filed: Oct. 28, 2010

(86) PCT No.: PCT/EP2010/066312
§ 371 (c)(1),
(2), (4) Date: Oct. 5, 2012

(87) PCT Pub. No.: WO2011/051365
PCT Pub. Date: May 5, 2011

(65) Prior Publication Data
US 2013/0023832 A1      Jan. 24, 2013

(30) Foreign Application Priority Data
Oct. 30, 2009 (EP) .................................... 09174662

(51) Int. Cl.
*A61M 5/00* (2006.01)
*A61M 5/24* (2006.01)
(Continued)

(52) U.S. Cl.
CPC .............. *A61M 5/24* (2013.01); *Y10T 29/49826* (2013.01); *Y10T 29/49764* (2013.01); *Y10T 29/49769* (2013.01); *A61M 5/3146* (2013.01); *A61M 5/315* (2013.01); *A61M 2005/2407* (2013.01); *A61M 2005/2492* (2013.01); *A61M 2207/00* (2013.01)
USPC ............................................ 604/208; 29/428

(58) Field of Classification Search
CPC ............. A61M 2005/2407; A61M 2005/2492; A61M 2207/00; A61M 5/24; A61M 5/3146; A61M 5/315
USPC ......................... 604/207–211, 232, 218, 181; 29/407.01, 407.04, 428
See application file for complete search history.

(56) References Cited

U.S. PATENT DOCUMENTS 2,855,928 A * 10/1958 Reynolds .................... 73/864.18
3,140,642 A *  7/1964 Nelson et al. .................... 92/248
4,333,456 A *  6/1982 Webb ............................ 604/121
(Continued)

FOREIGN PATENT DOCUMENTS

WO      WO2009095332      *  8/2009      ............ A61M 5/315

OTHER PUBLICATIONS

International Preliminary Report on Patentability for Int. App. No. PCT/EP2010/066312, mailed May 10, 2012.

*Primary Examiner* — Kami A Bosworth
*Assistant Examiner* — Imani Hayman
(74) *Attorney, Agent, or Firm* — McDonnell Boehnen Hulbert & Berghoff LLP

(57) ABSTRACT

A drug delivery device for dispensing of a dose of a medicinal product, comprising a holder (14) for a product-containing cartridge (16), the cartridge (16) having a piston (18) slidably arranged therein in an axial direction, a piston rod (12) to be operably engaged with the cartridge's piston (18) for dispensing of a dose of the medicinal product, and at least one spacer (20) being selected according to a relative distance between piston (18) and piston rod (12) and being disposed between the piston rod (12) and the piston (18) for eliminating axial clearance between piston (18) and piston rod (12).

12 Claims, 4 Drawing Sheets

Figure 1:
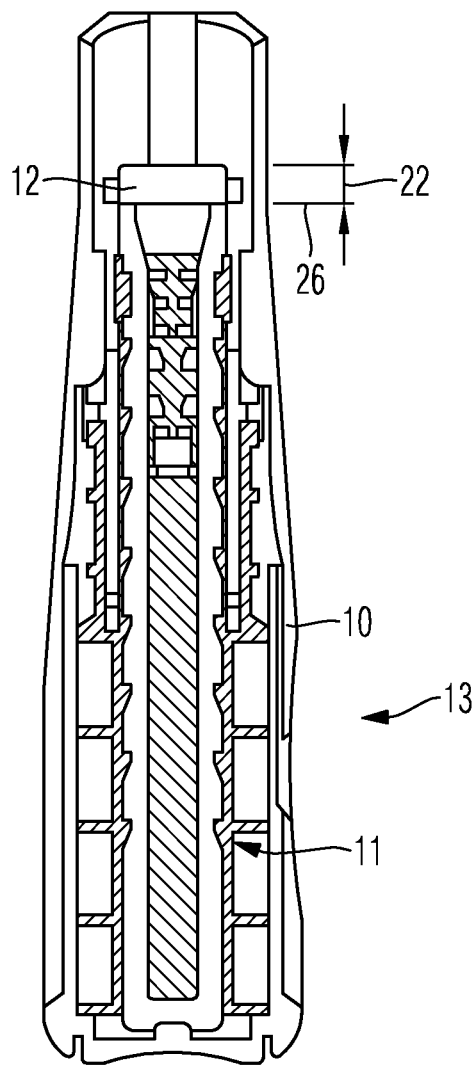

(51) Int. Cl.
*A61M 5/31* (2006.01)
*A61M 5/315* (2006.01)

(56) References Cited

U.S. PATENT DOCUMENTS

| | | | |
|---|---|---|---|
| 4,872,370 A * | 10/1989 | Benton et al. | 74/579 E |
| 5,007,904 A | 4/1991 | Densmore et al. | |
| 5,135,512 A * | 8/1992 | Mazurik et al. | 604/228 |
| 5,865,805 A | 2/1999 | Ziemba | |
| 6,196,999 B1 | 3/2001 | Goethel et al. | |
| 6,569,126 B1 * | 5/2003 | Poulsen et al. | 604/207 |
| 2011/0046567 A1 * | 2/2011 | Radmer et al. | 604/218 |
| 2011/0088493 A1 * | 4/2011 | Blumentritt et al. | 73/864.17 |

* cited by examiner

DRUG DELIVERY DEVICES AND METHOD OF ASSEMBLY

CROSS REFERENCE TO RELATED APPLICATIONS

The present application is a 35 U.S.C. 371 National Application of PCT/EP2010/066312 filed Oct. 28, 2010, which claims priority to European Patent Application No. 09174662.8, Oct. 30, 2009, the entire contents of which are incorporated entirely herein by reference.

This invention relates to a drive mechanism for a drug delivery device that allows a user to select single or multiple doses of an injectable medicinal product and to dispense the set dosage of the product and to apply said product to a patient, preferably by injection. In particular, the present invention relates to such devices, which are handled by the patients themselves.

Drug delivery devices allowing for multiple dosing of a required dosage of a liquid medicinal product and further providing administration of such liquid drug to a patient, are as such well-known in the prior art. Generally, such devices have substantially the same purpose as that of an ordinary syringe.

Drug delivery devices of this kind have to meet a number of user specific requirements. For instance in case of those with diabetes, many users will be physically infirm and may also have impaired vision. Therefore, these devices need to be robust in construction, yet easy to use, both in terms of the manipulation of the parts and understanding by a user of its operation. Further, the dose setting must be easy and unambiguous and where the device is to be disposable rather than reusable, the device should be inexpensive to manufacture and easy to dispose. In order to meet these requirements, the number of parts and steps required to assemble the device and an overall number of material types the device is made from have to be kept to a minimum.

Typically, the medicinal product to be administered is provided in a cartridge having a moveable piston or bung mechanically interacting with a piston rod of a drive mechanism of the drug delivery device. By applying thrust to the piston in distal direction, a certain and pre-defined amount of the medicinal fluid is expelled from the cartridge.

Due to inevitable manufacturing tolerances there may for instance arise axial clearance between a cartridge's piston and the piston rod. Typically, prior to a primary use of the device, an end-user has to conduct a so-called priming of the drive mechanism in order to ensure, that already with an initial dose setting and a subsequent dose dispensing step, an accurate amount of the medicinal product is disposed in a predefined way.

Since a self-administering user might be physically infirm, it is desirable to simplify or even to entirely eliminate the need for such a user-conductible priming procedure.

Document U.S. Pat. No. 6,196,999 B1 for instance discloses a coupling mechanism, wherein a syringe plunger coupling element having the form of a rearwardly extending cylindrical extension is centrally located on a rearward face of a syringe plunger. This coupling element contains an interior T-shaped cavity, wherein the walls of said cavity are knurled to aid the grip of the coupling mechanism. The coupling mechanism is located on the forward end of a plunger drive ram proximate to the syringe plunger and is in the form of two pawls. These pawls are biased away from the plunger drive ram's axis of symmetry by means of springs. Operation of a motor advances the drive ram forwardly along its longitudinal axis to move the pawls of the coupling mechanism toward and inter engagement with the cylindrical extension of the syringe plunger.

As the advancing pawls initially enter the cavity of plunger extension, their forward ends are forced toward one another by the walls of the cavity, overcoming the outward bias of the springs. In order to eliminate an initial clearance between plunger and drive ram, the pawls have to fully enter the cavity to grip the knurled wall of the cavity. Henceforward, the syringe plunger and drive ram will move in a cooperated motion.

These known solution features the drawback, that the piston rod has to be axially shifted for eliminating axial clearance between piston rod and piston. In know embodiments of drug delivery devices axial clearance- and backlash elimination implies to bring the piston rod in direct abutment position with a cartridge's piston. However, such axial displacement of the piston rod is regarded as disadvantageous, because it typically involves a respective actuation of dose setting or dose dispensing means by the user.

It is therefore an object of the present invention to provide a drive mechanism for a drug delivery device featuring improved and facilitated clearance and manufacturing tolerance elimination. It is a further object of the invention to make a priming procedure to be conducted by the end user redundant. The invention further focuses on improvements related to patient safety and intends to simplify the general device handling. It is a further object of the invention, to provide a simple and easy to assemble clearance elimination which is particularly inexpensive to realize and which implies only minor amendments to an existing design of the drug delivery device and/or its components.

The present invention provides a drug delivery device for dispensing of a dose of a medicinal product.

The terms "drug" or "medicinal product", as used herein, preferably mean a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl- ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4 (1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4 (1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2) 25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2) 25, Asp28] Exendin-4(1-39)-(Lys)6-NH2;
or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

The drug delivery device comprises a holder for a product-containing cartridge, such like a carpule, an ampoule or a comparable syringe-like container. Said cartridge comprises a piston being slidably arranged therein in an axial direction. Upon exertion of distally directed thrust, the piston is displaced in distal direction and a pre-defined dose of the typically liquid medicinal product can be expelled from the cartridge accordingly. The drug delivery device further comprises a drive mechanism for axially displacing a piston rod, which is to be operably engaged with the cartridge's piston. By means of the piston rod, dose-dispensing thrust can be applied to the cartridge's piston.

The piston rod and the drive mechanism are typically to be arranged and assembled inside a housing, wherein in a final assembly configuration of the drug delivery device, the housing itself is to be interconnected with a cartridge holder. For the purpose of eliminating axial clearance between piston and piston rod, at least one spacer is selected according to a relative distance between piston and piston rod. Said distance spacer, typically having the shape and function of a shim, is disposed between the piston and the piston rod.

Depending on the respective size and magnitude of axial clearance between piston and piston rod, said spacer is typically selected from a set of spacers of varying axial dimension. Said at least one spacer serves to bridge or to fill the axial gap which would otherwise arise, when cartridge holder and housing are mutually interconnected in a final step of assembly.

By appropriately selecting and arranging a particular distance spacer between piston and piston rod, a substantially clearance-free effective abutment of piston and piston rod can be reached upon final assembly of the drug delivery device, i.e. when housing and cartridge holder are mutually interconnected and fixed with respect to each other. In this way, a priming procedure generally becomes superfluous and the drug delivery device is ready for its first use upon completion of an assembly procedure.

According to a preferred embodiment of the invention, the at least one spacer is selected from a set of spacers having different axial dimensions. Said at least one spacer is selected according to an actually measured and/or determined and/or estimated axial clearance or gap size between piston rod and piston in the device's final assembly configuration. The at least one spacer is typically individually selected for each combination of pre-configured housing assembly and/or cartridge holder assembly. In this way, production and/or assembling tolerances can be effectively compensated by individually choosing and selecting an appropriately sized distance spacer.

In a further preferred embodiment, the at least one spacer is disposed at a distal end face of the piston rod and/or at a proximal end face of the piston of the cartridge. Hence, the at least one spacer is preferably attached to the piston or to the piston rod in a pre-assembly configuration of the drug delivery device, in which cartridge holder and housing are not yet interconnected. In said pre-assembly configuration, the piston rod and drive mechanism are pre-assembled in the housing and a cartridge is pre-assembled in the cartridge holder.

Depending on the orientation of the cartridge holder sub-assembly or the housing sub-assembly during a final step of assembly, it might be sufficient to loosely arrange the at least one spacer on top of a respective end face of piston or piston rod.

Preferably, the at least one spacer is undetachably attached to either the piston rod and/or to the piston of the cartridge. The spacer may be adhesively attached to said proximal or distal end faces, allowing for a flexible and universal handling of the respective sub-assembly of the drug delivery device.

It is also conceivable, that both, the end face of the piston rod and the respective end face of the piston or its pressure piece are provided with at least one distance spacer, typically having a shim- or disk-like contour.

Depending on the overall dimensions of the drug delivery device and its components, the axial dimension of the at least one spacer of the provided set of spacers can be as small as 1 mm, 0.8 mm, 0.6 mm, 0.4 mm, 0.2 mm or even smaller than 0.2 mm. Furthermore, it is conceivable, that not only one but several distance spacers are disposed on a respective end face of piston rod and/or piston. In this way, even axial gaps larger than 1 mm can be effectively compensated and eliminated. Moreover, by making use of a set of spacers having axial dimensions of for instance 0.1 mm, 0.2 mm, 0.5 mm, almost any axial gap size between 0.1 and 1 mm can be effectively compensated for in steps of 0.1 mm by a respective combination of available distance spacers.

According to another independent aspect, the present invention also relates to a method of assembly of a drug delivery device, wherein the device is adapted for dispensing of a pre-defined dose of a medicinal product, such like heparin or insulin. The method of assembly comprises the steps of determining an axial position of a proximal end face of a piston of a cartridge pre-assembled in a cartridge holder. In a similar way, also an axial position of a distal end face of a piston rod of a drive mechanism pre-assembled in a housing is determined. By means of the determined or actually measured axial positions of piston and piston rod, the size of axial clearance between the piston and the piston rod can be determined or at least estimated.

Axial clearance or a respective axial gap will arise, if cartridge holder and housing of the drug delivery device were assembled in their final assembly configuration. By means of separately determining respective axial positions of piston and piston rod relative to cartridge holder and housing, the resulting axial clearance can already be determined before housing and cartridge holder are mutually interconnected. Depending on the determined or estimated size or magnitude of axial clearance between piston and piston rod, at least one spacer is selected from a set of differently sized spacers. The selected spacer of appropriate size is then arranged between the piston and the piston rod during or before final assembly of the drug delivery device.

Preferably, said at least one spacer is attached to the distal end face of the piston rod and/or to the proximal end face of the piston. Attachment or displacement of the at least one spacer can be embedded in a mass production process before pre-assembled housing and cartridge holder are mutually interconnected.

According to a preferred embodiment, the axial position of the distal end face of the piston rod is determined with respect to a selected reference point of the housing.

Accordingly, also the axial position of the proximal end face of the piston is determined with respect to a selected reference point of the cartridge holder. Hence, axial positions of piston and piston rod are preferably determined with respect to the geometry of a housing component or a cartridge holder.

In this context, it is of advantage, when said selected reference points of housing and/or cartridge holder substantially coincide with axial positions of fastening means adapted to mutually interconnect housing and cartridge holder. Housing and cartridge holder are typically to be interconnected in an interleaved arrangement, wherein an insert portion of cartridge holder or housing is axially inserted into a corresponding receptacle of housing or cartridge holder. Insert portion and/or receptacle may additionally comprise mutually corresponding fastening or pre-fixing means, such as for instance mutually matching through openings and respective catch- or latch elements.

Furthermore, it is also conceivable, that cartridge holder or housing component, typically of substantially cylindrical shape, comprise a bearing or an abutment shoulder acting as a stopper and being adapted to delimit a mutually inserting movement of housing and cartridge holder. A free end of either receptacle and/or insert portion may axially abut with a respective bearing of insert portion and/or receptacle, thereby defining the final assembly configuration of the drug delivery device. By measuring the distance between end faces of piston rod and piston with respect to a free end or with respect to an abutment shoulder of insert portion or receptacle of housing or cartridge holder, the axial clearance between piston rod and piston when reaching the final assembly position can be precisely determined.

In a further preferred embodiment of the invention, the axial position of the piston and/or of the piston rod is determined by means of a tactile probe or by means of an optical sensor arrangement in a contact-less way.

In the event that also the absolute positions of selected reference points of cartridge holder and/or housing vary in a mass production process, it may be of advantage to make use of digital image processing in order to precisely determine axial distance between end faces of piston or piston rod and selected reference points.

According to a further preferred embodiment, the cartridge is disposed in the cartridge holder to build a cartridge holder sub-assembly. Accordingly, also the drive mechanism with its piston rod is disposed in the housing to build a housing sub-assembly. Both assemblies are assembled before axial positions of piston and/or piston rod are determined.

According to another embodiment of the invention, the cartridge holder and the housing are undetachably interconnected by means of welding or bonding or by means of friction- or positive locking fastening means. Housing and cartridge holder are preferably interconnected after an appropriate distance spacer has been attached to at least one end face of piston or piston rod. By mutually assembling and subsequently interconnecting of housing and cartridge holder, axial clearance or backlash otherwise present in the drive mechanism can be effectively and durably eliminated and the device is prepared for an initial dose setting and dispensing as soon as the device assembly has been completed.

It is further conceivable for the present invention, that pre-assembled sub-assemblies, namely cartridge holder sub-assembly and/or housing sub-assembly are selected from a set of respective sub-assemblies for the purpose of minimizing axial clearance between piston and piston rod. Here, axial position of a piston rod's distal end face with respect to the housing is determined. Similarly, for a set of cartridge holder sub-assemblies, a respective measurement can be conducted for determination of axial position of the piston. Any set of actually measured cartridge holder sub-assemblies or housing sub-assemblies can thus be classified with respect to the measured axial position of piston rod's and piston's end faces. By making use of actually measured or otherwise determined positions of respective end faces, pairs of sub-assemblies can be selected for assembling a drug delivery device in such a way, that axial clearance between piston and piston rod is minimized or even eliminated. Depending on given manufacturing and assembly tolerances, axial clearance may even be eliminated solely by appropriately selecting mutually matching housing sub-assemblies and cartridge holder sub-assemblies. In this way, interposition of a distance spacer may even become superfluous.

Furthermore, in an alternative embodiment, the at least one spacer does not necessarily have to be disposed between piston and piston rod. Also other positions and locations, such as an arrangement between housing and cartridge holder are conceivable. In another example, the spacer may even be used to vary the axial position of the cartridge with respect to the cartridge holder. In this way, the spacer could even be disposed between a distal neck portion of the cartridge holder and the cartridge itself prior to an assembly of the cartridge inside the cartridge holder.

It will be apparent to those skilled in the art, that various modifications and variations can be made to the present invention without departing from its spirit and scope. Further, it is to be noted, that any reference signs used in the appended claims are not to be construed as limiting the scope of the present invention.

Figure 2:
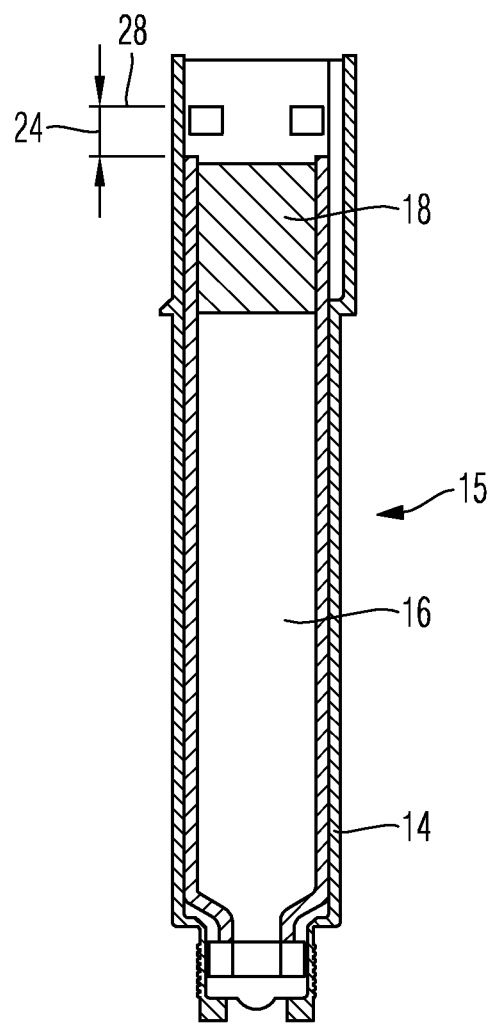
Figure 3:
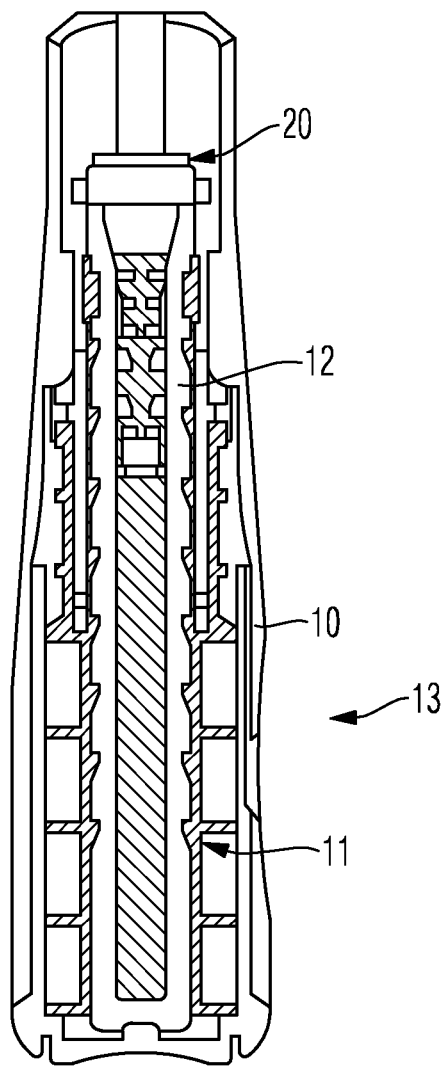
Figure 4:
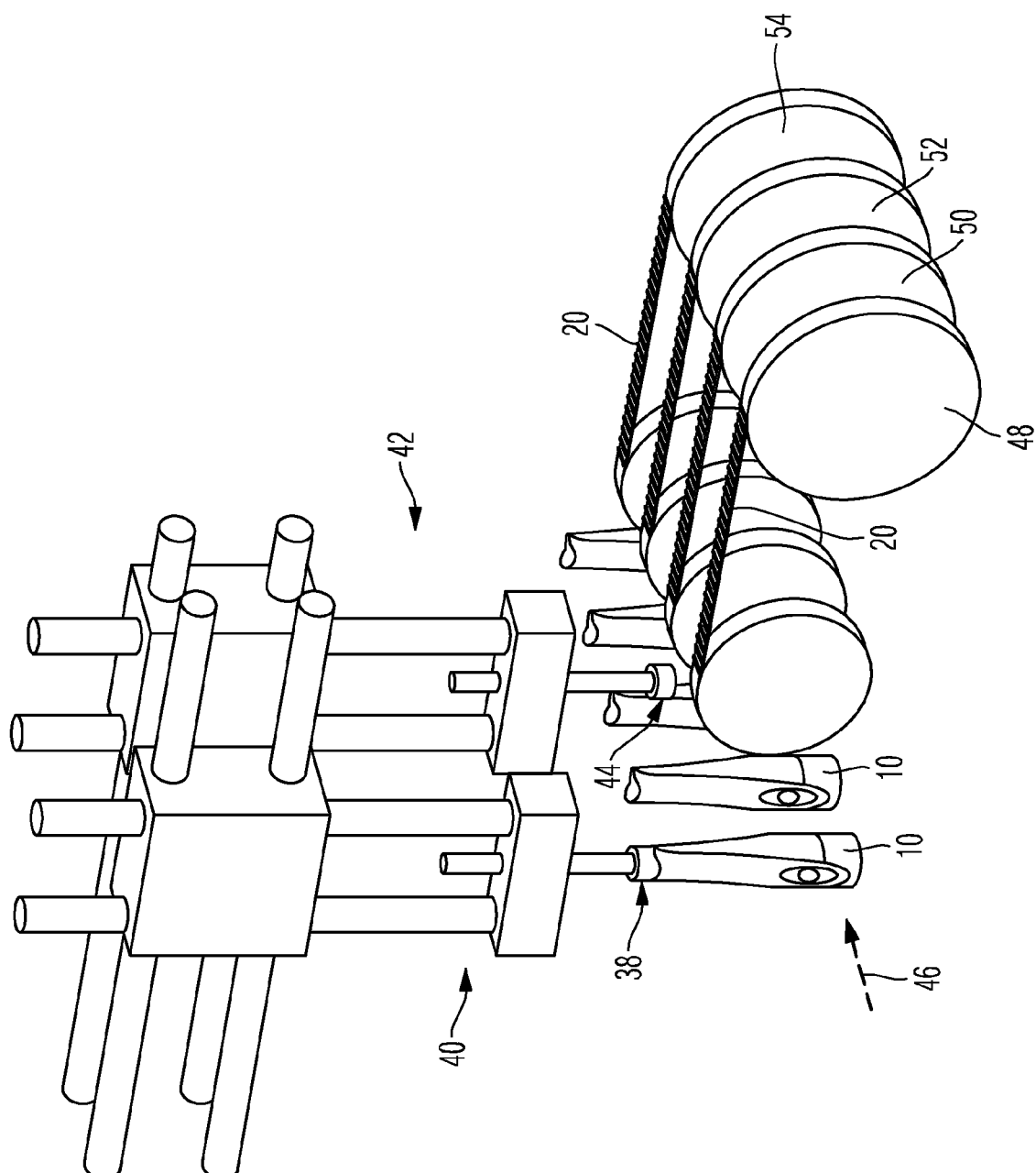
Figure 5:
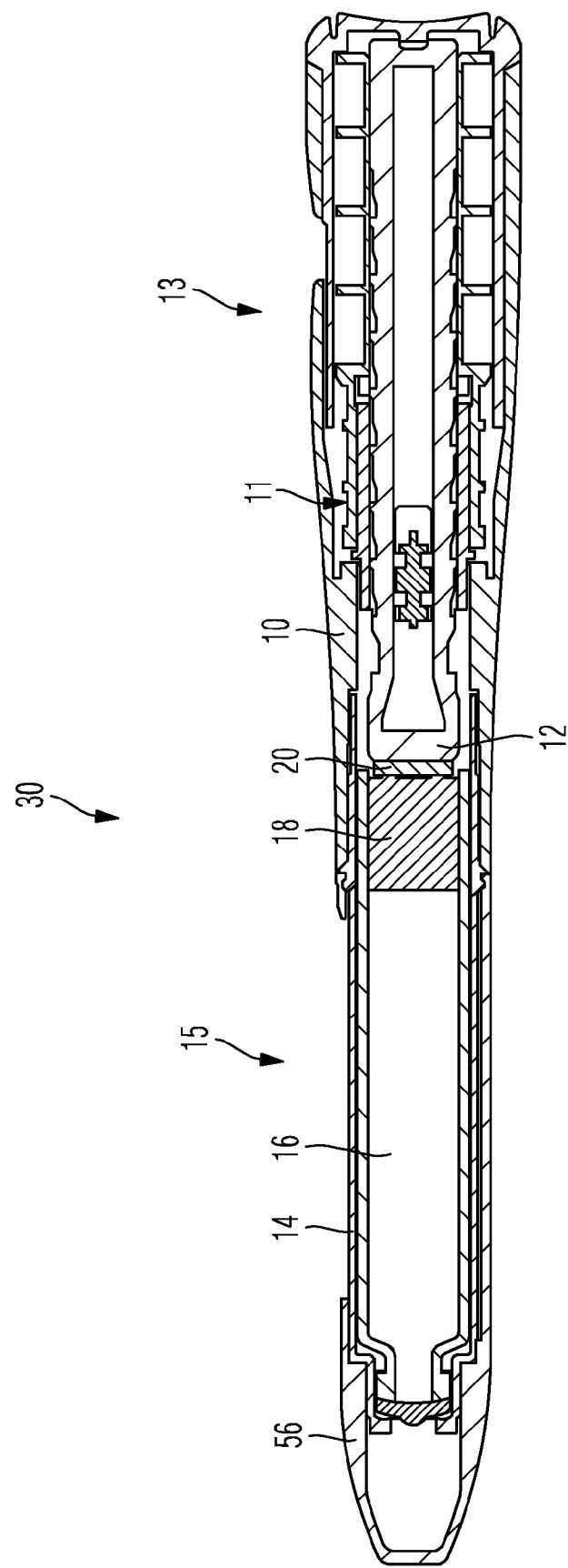

Without limitation, the present invention will be explained in greater detail below in connection with preferred embodiments and with reference to the drawings in which:

FIG. 1 schematically depicts a housing sub-assembly in cross sectional illustration, FIG. 2 schematically shows a cartridge holder sub-assembly in cross sectional illustration, FIG. 3 illustrates the housing sub-assembly with a distance spacer attached to the piston rod, FIG. 4 schematically illustrates a production line for determining axial position of piston rod and for providing distance spacers of variable size and FIG. 5 shows an assembled drug delivery device in longitudinal cross section.

In FIGS. 1 and 2 a housing sub-assembly 13 and a cartridge holder sub-assembly 15 are illustrated, respectively. The housing sub-assembly 13 comprises a housing 10 receiving a drive mechanism 11 of a drug delivery device. The drive mechanism 11 and its piston rod 12 are pre-assembled in said housing 10.

In FIG. 2, a cartridge holder 14 is illustrated adapted to receive a cartridge 16 containing a medicinal product, such like a fluid drug, e.g. insulin or heparin. The cartridge 16 further comprises an axially displaceable piston 18, which is to be displaced in distal direction by means of the distally advancing piston rod 12 for expelling a pre-defined amount of the medicinal product.

As shown in FIG. 2, a proximal and upper end section of the cartridge holder 14 is designed as insert piece or insert section to be received by a corresponding receptacle located at the distal and upper end section of the housing 10 according to FIG. 1. Hence, housing 10 and cartridge holder 14 can be assembled in an interleaved and in an at least partially overlapping arrangement. In a final assembly configuration, which is illustrated in FIG. 5, a distal end face of the piston rod 12 abuts against a proximal end face of the piston 18.

In order to compensate for inevitable production and assembly tolerances, the axial position of the piston rod 12 and/or a respective axial position of the piston 18 is actually measured or determined prior to mutual interconnection of sub-assemblies 13, 15.

Typically, the axial position of the piston rod's distal end face is measured by way of a distance 22 to a selected reference point 26. Similarly, also the axial position of the piston's proximal end face is determined by measuring the distance between said proximal end face and a selected reference point 28 of the cartridge holder 14. In this way, axial positions or distances 22, 24 of mutually abutting end faces of piston rod 12 and piston 18 can be individually and separately determined for each sub-assembly before the housing sub-assembly 13 and the cartridge holder sub-assembly 15 are finally interconnected.

Having knowledge of relative axial positions or distances 22, 24, the size of axial clearance or the size of an arising axial gap between piston rod 12 and piston 18 can be individually determined for each drug delivery device. According to the determined size of said axial gap, a correspondly sized distance spacer 20 can be attached to either piston rod 12 or piston 18 before the two sub-assemblies 13, 15 are mutually interconnected. By selecting an appropriately sized distance spacer 20 or shim, axial clearance between piston rod 12 and piston 18 can be effectively eliminated. In this way it can be substantially ensured, that the piston rod's distal end face effectively abuts against the proximal end face of the piston 18 when a final assembly configuration of housing 10 and cartridge holder 14 has been reached. In this way, a priming procedure to be conducted by the end user prior to a first use of the drug delivery device can be entirely compensated and eliminated.

In FIG. 4, a system for manufacturing and assembling a drug delivery device is partially illustrated. Here, a series of housing sub-assemblies 10 is stepwise or constantly moved along a production line 46. A measuring unit 40 is adapted to determine the axial position of the piston rod 12 or its distance 22 to a selected reference point, either by means of a tactile or contactless measuring procedure way, e.g. by making use of an optical measurement unit, such like an optical sensor 38.

In a similar but not illustrated way, also the axial positions of pistons 18 of a series of cartridge holder sub-assemblies 15, each of which to be interconnected with a particular housing sub-assembly 13 is determined in a similar way.

Depending on the obtained axial positions of piston rod 12 and piston 18, at least one or several distance spacers 20 of appropriate size and shape are selected. Said distance spacers 20 are provided by a feeding unit comprising four different feeding stations 48, 50, 52, 54, each of which being adapted to provide distance spacers 20 of different axial size or dimensions. An assembling unit 42 is adapted to take and/or to select an appropriately sized spacer 20 from either one of the feeding stations 48, 50, 52, 54. Said selecting and assembling unit 42 further comprises a feeding head 44, adapted to select a particular spacer 20 and to arrange the selected spacer 20 onto the distal end face of the piston rod 12. Preferably, either piston rod 12 or said distance spacer 20 is provided with an adhesive preventing unintended detachment of the distance spacer in the course of further assembly.

The distance spacers 20 as provided by the separate feeding stations 48, 50, 52, 54 may comprise axial sizes of e.g. 0.2 mm, 0.4 mm, 0.6 mm, 0.8 mm and so on. Alternatively, it is also conceivable, that the axial size of said spacers equal for instance 0.1 mm, 0.2 mm, 0.5 mm or 1.0 mm. It is even conceivable, to make use of a combination of several distance spacers 20 to be positioned on top of each other. In this way, a large range of axial gap sizes can be precisely eliminated.

FIG. 5 finally illustrates the assembled drug delivery device 30, wherein an appropriate distance spacer 20 is positioned and squeezed between the distal end face of the piston rod and the piston's 20 proximal end face. Also, housing 10 and cartridge holder 14 are mutually positively engaged, e.g. by means of a snap fit. Hence, cartridge holder 14 and housing 10 are therefore arranged in at least partially nested or interleaved way.

REFERENCE NUMERALS 10 housing
11 drive mechanism
12 piston rod
13 housing sub-assembly
14 cartridge holder
15 cartridge holder sub-assembly
16 cartridge
18 piston
20 spacer
22 axial distance
24 axial distance
26 reference point
28 reference point
30 drug delivery device
38 sensor
40 measuring unit
42 selecting and assembling unit
44 feeding head
46 production line
48 feeding station
50 feeding station
52 feeding station
54 feeding station
56 cap

The invention claimed is:

1. A drug delivery device for dispensing of a dose of a medicinal product, comprising:
    a holder for a product-containing cartridge, the cartridge having a piston slidably arranged therein in an axial direction, and
    a piston rod to be operably engaged with the cartridge's piston for dispensing of a dose of the medicinal product, wherein
    at least one spacer selected according to a relative distance between the piston and the piston rod is disposed between the piston rod and the piston for eliminating axial clearance between piston and piston rod, and
    wherein the at least one spacer is selected from a set of spacers having different axial dimensions and
    wherein the at least one spacer is selected according to an actually measured or determined or estimated gap size between the piston rod and the piston in the device's final assembly configuration.

2. The drug delivery device according to claim 1, wherein in a pre-assembly configuration, the at least one spacer is disposed at a distal end face of the piston rod or at a proximal end face of the piston of the cartridge.

3. The drug delivery device according to claim 2, wherein the at least one spacer is adhesively attached to the piston rod or to the piston of the cartridge.

4. The drug delivery device according to claim 1, wherein the axial dimension of the at least one spacer is smaller than or equal to 1 mm, 0.8 mm, 0.6 mm, 0.4 mm or 0.2 mm.

5. A method of assembly of a drug delivery device being adapted for dispensing of a dose of a medicinal product, comprising the steps of:
    determining an axial position of a proximal end face of a piston of a cartridge pre-assembled in a cartridge holder,
    determining an axial position of a distal end face of a piston rod of a drive mechanism pre-assembled in a housing,
    determining or estimating the size of axial clearance between the piston and the piston rod if cartridge holder and housing were assembled, selecting at least one spacer from a set of differently sized spacers with respect to the determined size of axial clearance and arranging the selected spacer between the piston and the piston rod.

6. The method according to claim 5, wherein the spacer is attached to the distal end face of the piston rod or to the proximal end face of the piston.

7. The method according to claim 5, wherein the axial position of the distal end face of the piston rod is determined with respect to a selected reference point of the housing or wherein the axial position of the proximal end face of the piston is determined with respect to a selected reference point of the cartridge holder.

8. The method according to claim 7, wherein selected reference points of housing or cartridge holder substantially coincide with the axial position of fastening means adapted to mutually interconnect housing and cartridge holder.

9. The method according to claim 5, wherein the axial position of the piston or of the piston rod is determined by means of a tactile probe or by means of an optical sensor arrangement.

10. The method according to claim 5, wherein the cartridge is disposed in the cartridge holder to form a cartridge holder sub-assembly and wherein a drive mechanism with a piston rod is disposed in the housing to form a housing sub-assembly before axial positions of the piston and the piston rod are determined.

11. The method according to claim 5, wherein the cartridge holder and the housing are undetachably interconnected by means of welding or bonding or by means of friction- or positive locking fastening means.

12. The method according to claim 9, wherein a cartridge holder sub-assembly or a housing sub-assembly are selected from a set of respective sub-assemblies for minimizing axial clearance between piston and piston rod.

* * * * *